United States Patent [19]
Pierce

[11] Patent Number: 5,090,806
[45] Date of Patent: Feb. 25, 1992

[54] METHOD AND APPARATUS FOR MEASURING THE COMPOSITION OF A ZINC PHOSPHATE COMPOUND

[75] Inventor: Brian M. Pierce, Moreno Valley, Calif.

[73] Assignee: Hughes Aircraft Company, Los Angeles, Calif.

[21] Appl. No.: 425,091

[22] Filed: Oct. 23, 1989

[51] Int. Cl.[5] ............................................. G01J 3/44
[52] U.S. Cl. .................................................. 356/301
[58] Field of Search ...................................... 356/301

[56] References Cited
U.S. PATENT DOCUMENTS
4,620,284  10/1986  Schnell et al. .................... 356/301

Primary Examiner—F. L. Evans
Assistant Examiner—K. P. Hantis
Attorney, Agent, or Firm—Michael W. Sales; Wanda K. Denson-Low

[57] ABSTRACT

A method and apparatus (66, 72, 74) is disclosed which allows for the measurement of a concentration of hopeite and phosphophyllite contained within a zinc phosphate coating material (64). Specifically, the method employs Raman spectroscopy and measures the aforementioned concentration in an on-line and non-contact manner.

2 Claims, 2 Drawing Sheets

METHOD AND APPARATUS FOR MEASURING THE COMPOSITION OF A ZINC PHOSPHATE COMPOUND

BACKGROUND OF THE INVENTION

1. Field of the Invention

This invention relates to a method and apparatus for measuring the composition of a zinc phosphate compound and, more particularly, to a method and apparatus for measuring the concentration of hopeite and phosphophyllite on an article of manufacture.

2. Discussion

Zinc phosphate compounds are used to coat steel parts of automobiles and other types of machinery thereby imparting a high degree of corrosion resistance to the same. The degree of corrosion resistance so imparted is usually dependent upon the concentration of hopeite and phosphophyllite contained within the zinc phosphate compound. Therefore precise measurements of these contained concentrations must continuously be made in order to ensure product quality. Such measurements are usually made during an assembly process of the component.

Current approaches used to determine this hopeite and phosphophyllite concentration include the SEM, ESCA, and Auger methodologies as well as x-ray diffractometry and similar techniques used to study the microscopic structure of surfaces. These techniques, while effective, involve some sort of special preparation of the vehicle or sample under study (e.g., the vehicle must be placed within a vacuum). Thusly, these techniques are not suitable for on-line or non-contact monitoring and therefore production time and resources are wasted during this testing time resulting in inefficient assembly processes.

SUMMARY OF THE INVENTION

According to the teachings of the present invention, the concentration of phosphophyllite and hopeite contained within a zinc phosphate coating compound may be measured optically, preferably by the technique of Raman spectroscopy.

Accordingly, Raman spectra are initially developed for pure phosphophyllitic and hopeite compounds and characteristic frequencies associated with each are developed. A calibration curve is then developed for a plurality of zinc phosphate coating compounds containing known concentrations of hopeite and phosphophyllite. These known concentrations are uniquely associated with either a height or an area of a spectral peak occurring at one of the characteristic frequencies. A Raman spectrum is then obtained for a zinc phosphate compound having an unknown concentration of hopeite and phosphophyllite and the height or area of the peak occurring at one of the aforementioned characteristic frequencies of hopeite and of phosphophyllite are then compared to the calibrated data. Such a comparison is seen to enable the determination of the contained concentration of hopeite and phosphophyllite within the compound.

It is therefore a feature of this invention to provide a method and apparatus for the non-contact and on line measurement of the concentration of hopeite and phosphophyllite contained within a zinc phosphate coating compound.

It is another feature of this invention to provide Raman Spectroscopy means to accomplish this on-line and non-contact measurement system and apparatus.

It is yet another feature of this invention to provide computer means to control the aforementioned Raman spectroscopy means, to store the aforementioned calibrated data, and to compare a measured signal height or area with the calibrated data.

These and other aspects, features, advantages, and objects of this invention will be more readily understood upon reviewing carefully the following detailed description taken in conjunction with the accompanying drawings and appended claims.

BRIEF DESCRIPTION OF THE DRAWINGS

The various advantages of the present invention will become apparent to those skilled in the art by reading the following specification and by reference to the drawings in which.

DESCRIPTION OF THE PREFERRED EMBODIMENT

Figure 1A:
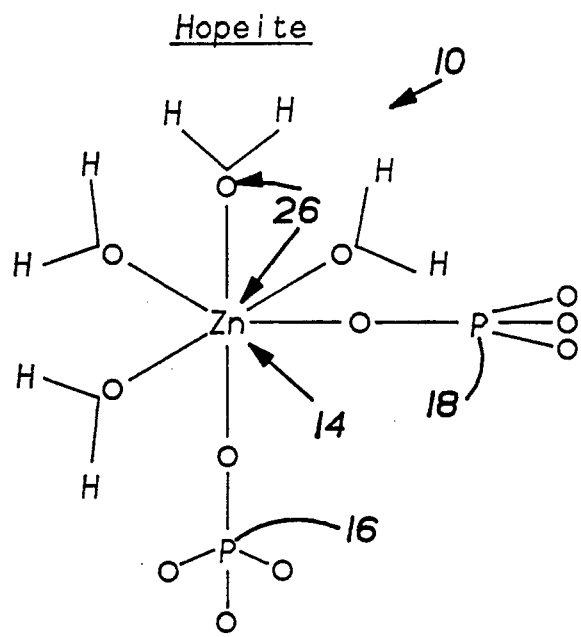
FIGS. 1 (A-B) are illustrations of the chemical bonding structure of hopeite and phosphophyllite.
Figure 1B:
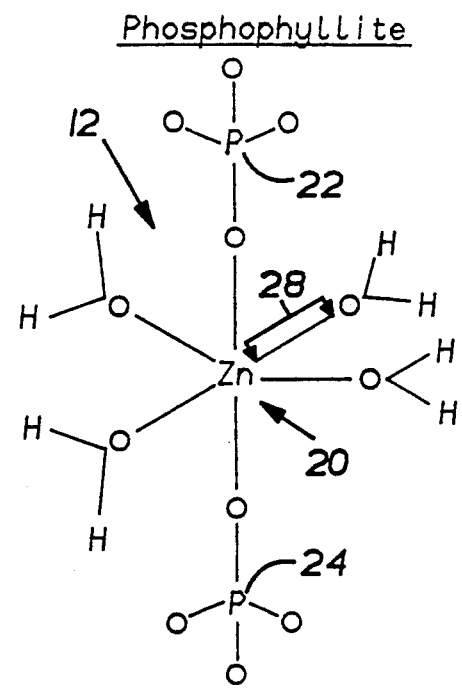

Turning now to FIGS. 1 (A-B), the octahedral chemical bonding structures of hopeite 10 and of phosphophyllite 12 are therein illustrated. Specifically, hopeite contains a $ZnO_2(H_2O)_4$ octahedral unit 14 bonded to phosphate groups 16 and 18. Phosphophyllite however, contains a $FeO_2(H_2O)_4$ octahedral unit 20 bonded to phosphate groups 22 and 24.

The average zinc to oxygen bond length 26 of hopeite material 10 is approximately 2.106A and the average iron to oxygen bond length 28 of phosphophyllite material 12 is approximately 2.130A. The masses of zinc and iron are known to be 65.38 and 55.847 amu respectively.

Thusly, the aforementioned mass difference, octahedral structural differences, and oxygen bonding length differences all co-operate to insure that the atomic vibrational characteristics of hopeite and phosphophyllite are different, thusly allowing the use of Raman spectroscopy to uniquely identify these materials.

The fundamental interaction defining Raman spectroscopy is the inelastic scattering of an incident photon by a material such that the difference in frequency between the frequencies of the incident and scattered photon is approximately equal to a vibrational frequency of the material. Photons scattered at different frequencies indicate different vibrational frequencies associated with the constituent compounds contained within the material. The intensity of the scattered photons at a given frequency is known to be proportional to the change in polarizability associated with the material vibration. This technique requires no special preparation of the material to be studied and has been found to be readily suited for non-contact and on-line measurement of various materials.

Figure 2A:
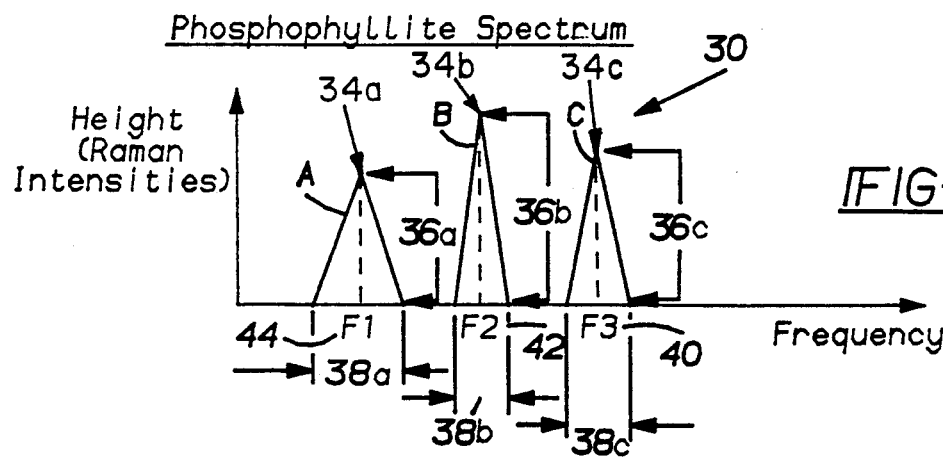
FIGS. 2 (A-B) are illustrations of a typical Raman spectrum associated with pure phosphophyllite and hopeite materials.
Figure 2B:
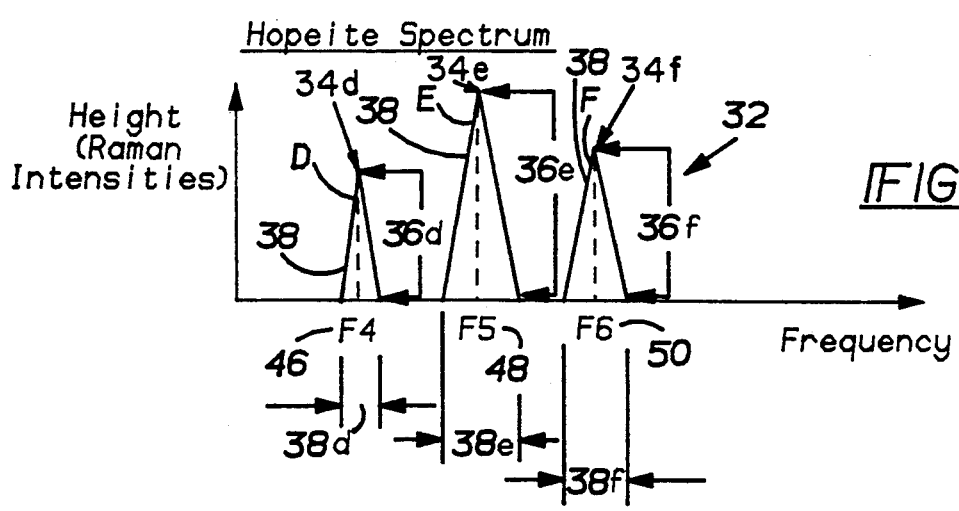

Referring now to FIGS. 2 (A-B), there is illustrated a Raman spectrum 30 of pure phosphophyllite material and a Raman spectrum 32 of pure hopeite material. These spectra both contain a plurality of peaks 34a-34f having heights 36(a)-(f) and defining areas 38(a)-(f) wherein areas 38(a)-(f) are centered around unique frequencies 40-50 respectively.

Frequencies 40, 42, and 44 are the characteristic frequencies of phosphophyllite and frequencies 46, 48, and 50 are the characteristic frequencies of hopeite. Characteristic frequencies 40, 42, and 44 uniquely identify phosphophyllite relative to hopeite since hopeite contains no peaks at these frequencies. Similarly, frequencies 46, 48 and 50 uniquely identify hopeite relative to phosphophyllite since phosphophyllite contains no peaks 34a-34c at these frequencies. Peaks 34a-34c occurring at frequencies 40, 42, or 44 thereby uniquely identify the presence of phosphophyllite and peaks 34d-34f occurring at frequencies 46, 48, or 50 uniquely identify the presence of hopeite within any material of interest.

It is known that the heights 36(a)-(f) or areas 38(a)-(f) of the peaks each indicate a concentration of phosphophyllite or hopeite within the characterized material. That is, the greater the height 36(a)-(f) or area 38(a)-(f) becomes, the more of the corresponding material (i.e. phosphophyllite or hopeite) is present within the compound of interest.

Figure 3:
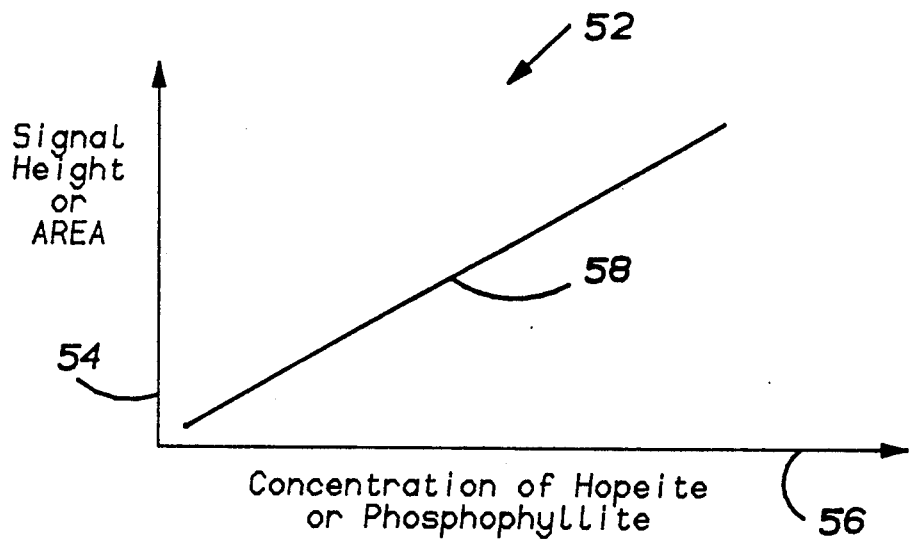
FIG. 3 is an illustration of a typical calibration curve developed and used by the preferred embodiment of this invention.

By measuring one of the heights 36(a)-(f) or one of the areas 38(a)-(f) of peaks 34a-34f at a given characteristic frequency associated with a plurality of known concentrations of phosphophyllite or hopeite, one may create a calibration graph 52 as illustrated in FIG. 3.

The vertical axis 54 of graph 52 contains a plurality of measured heights 36(a)-(f) or areas 38(a)-(f) at a given characteristic frequency. The horizontal axis 56 represents a plurality of known concentrations of either hopeite or phosphophyllite.

Calibration curve 58 may be created by joining together all points representing a height 36(a)-(f) or area 38(a)-(f) of a known concentration of hopeite or phosphophyllite. Both hopeite and phosphophyllite, in the preferred embodiment of this invention, have their own characteristic curves 58.

Figure 4:
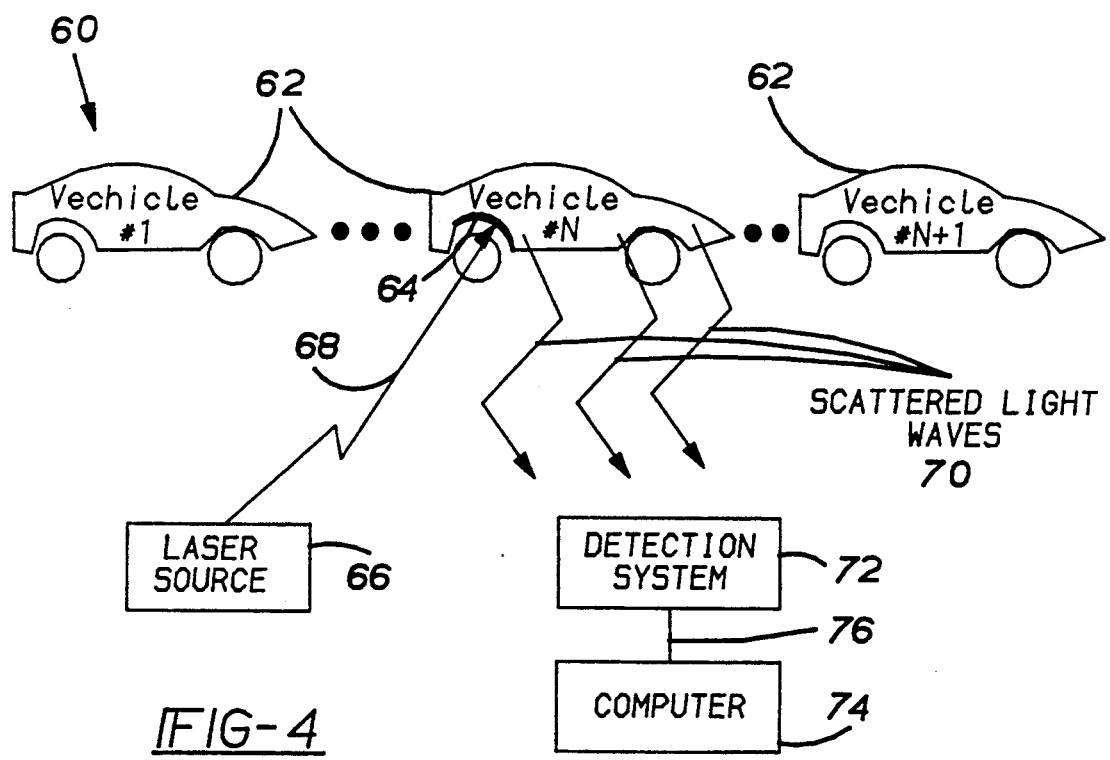
FIG. 4 is an illustration of the use of the preferred embodiment of this invention within an automobile assembly line.

Referring now to FIG. 4, there is illustrated a vehicle assembly line 60 having a plurality of vehicles 62 wherein said vehicles 62 contain a corrosion resistant zinc phosphate coating 64 having a concentration of hopeite and phosphophyllite and wherein said vehicles 62 move along the line 60 during an assembly process.

Once the calibration curve 58 has been generated for both hopeite and phosphophyllite, Raman spectroscopy may be used to measure the concentration of hopeite and phosphophyllite contained within coating 64. That is, laser source 66 is deployed such that light energy in the form of photons 68 are sequentially directed to each of the moving vehicles 62 as they pass by. Each of the vehicles 62 then scatters photon energy 68 and produces scattered light energy waves 70 which are made to impinge a standard Raman spectrum detection system 72.

Detection system 72 is electronically coupled to a digital computer 74 (i.e. an IBM AT type) by signal on line 76 which represents the occurrence of peaks 34 at characteristic frequencies of material 64. Computer 74 is made to store the previously generated calibration curve 58 associated with both hopeite and phosphophyllite and compares curve 58 with the height 36(a)-(f) or area 38(a)-(f) of a single peak at a single characteristic frequency of hopeite and of phosphophyllite associated with coating 64. This comparison yields an approximation, by standard linear mathematical interpolation techniques, of the concentration of hopeite and of phosphophyllite contained within material 64. Computer 74 employs standard Raman spectroscopy detection software.

It should be appreciated that the use of the aforementioned Raman spectroscopy means for measuring a concentration of hopeite and phosphophyllite within a vehicle coating material 64 does not require any special preparation of vehicle 62 nor does it require contact with the same. The technique of the preferred embodiment of this invention allows a vehicle or assembly process to be uninterrupted while such testing is occurring and therefore greatly reduces resource waste.

While it will be apparent that the preferred embodiment of the invention disclosed is well calculated to provide the advantages and features above stated, it will be appreciated that the invention is susceptible to modification, variation, and change without departing from the proper scope and fair meaning of the subjoined claims.

What is claimed is:

1. A method for measuring unknown concentrations of a first and second substance which make up a material, the concentration of said first and second substances being indicated by measuring the amplitude of RAMAN frequencies for said material, said method comprising:

determining a first unique RAMAN frequency for said first substance, said first frequency not present for said second substance;

determining a second unique RAMAN frequency of said second substance, said second frequency not present for said first substance;

measuring the amplitude of said first RAMAN frequency for a plurality of known concentrations of said first substance to generate a first calibration curve;

measuring the amplitude of said second RAMAN frequency for a plurality of known concentration of said second substance to generate a second calibration curve;

measuring the amplitude of the first and second RAMAN frequencies for the material to generate first and second comparison values;

comparing the first comparison value to the first calibration curve to indicate the concentration of the first substance present in said material; and comparing the second comparison value to the second calibration curve to indicate the concentration of the second substance present in said material.

2. The method of claim 1 wherein said first substance is hopeite and said second substance is phosphophyllite.

* * * * *